United States Patent
Waterson et al.

(10) Patent No.: US 9,845,375 B2
(45) Date of Patent: Dec. 19, 2017

(54) ADDITIVES FOR FUELS AND OILS COMPRISING FUNCTIONALISED DIBLOCK COPOLYMERS

(71) Applicant: Infineum International Limited, Abingdon (GB)

(72) Inventors: Carl Waterson, Wrexham (GB); Kenneth Lewtas, Wantage (GB); Peter Scott, Coventry (GB); Christopher J. Kay, Coventry (GB); Giles W. Theaker, Abingdon (GB); Peter M. Wright, Mountainside, NJ (US)

(73) Assignee: INFINEON INTERNATIONAL LIMITED (GB)

( * ) Notice: Subject to any disclaimer, the term of this patent is extended or adjusted under 35 U.S.C. 154(b) by 0 days.

(21) Appl. No.: 15/368,868

(22) Filed: Dec. 5, 2016

(65) Prior Publication Data
US 2017/0081458 A1    Mar. 23, 2017

Related U.S. Application Data

(62) Division of application No. 13/936,539, filed on Jul. 8, 2013, now Pat. No. 9,540,583.

(51) Int. Cl.
| | |
|---|---|
| C10M 145/14 | (2006.01) |
| C08F 297/02 | (2006.01) |
| C10L 1/10 | (2006.01) |
| C07C 15/00 | (2006.01) |
| C10M 101/02 | (2006.01) |
| C10L 1/196 | (2006.01) |
| C10L 1/16 | (2006.01) |
| C10M 143/10 | (2006.01) |
| C10M 143/12 | (2006.01) |

(52) U.S. Cl.
CPC ............ *C08F 297/02* (2013.01); *C10L 1/165* (2013.01); *C10L 1/1658* (2013.01); *C10L 1/1963* (2013.01); *C10M 143/10* (2013.01); *C10M 143/12* (2013.01); *C10M 145/14* (2013.01); *C10L 2250/04* (2013.01); *C10L 2270/026* (2013.01); *C10M 2205/022* (2013.01); *C10M 2205/06* (2013.01); *C10M 2209/084* (2013.01); *C10N 2220/021* (2013.01); *C10N 2230/02* (2013.01)

(58) Field of Classification Search
CPC ... C10N 2230/02; C08F 291/00; C08F 257/02
USPC ......... 508/591; 44/300; 525/242; 585/11, 24
See application file for complete search history.

(56) References Cited

U.S. PATENT DOCUMENTS

| | | | |
|---|---|---|---|
| 5,185,401 A | 2/1993 | Rendina et al. | |
| 7,018,962 B2* | 3/2006 | Bloch | C10M 169/04 508/591 |
| 2010/0152370 A1* | 6/2010 | Steinhauser | C08L 19/006 524/572 |

FOREIGN PATENT DOCUMENTS

| | | | | |
|---|---|---|---|---|
| EP | 0522729 A1 | 1/1993 | | |
| EP | 1500691 A2 | 1/2005 | | |
| JP | EP 0522729 A1 * | 1/1993 | ............ | C08F 255/02 |
| WO | WO-87/03603 A1 | 6/1987 | | |

* cited by examiner

*Primary Examiner* — Vishal Vasisth

(57) ABSTRACT

Concentrates containing specific functionalized diblock copolymers serve as effective additives for improving the cold flow behavior of fuels and oils, the copolymers being derived from a terminally-unsaturated intermediate polymer obtained via a metallocene process involving hydrogen.

24 Claims, 1 Drawing Sheet

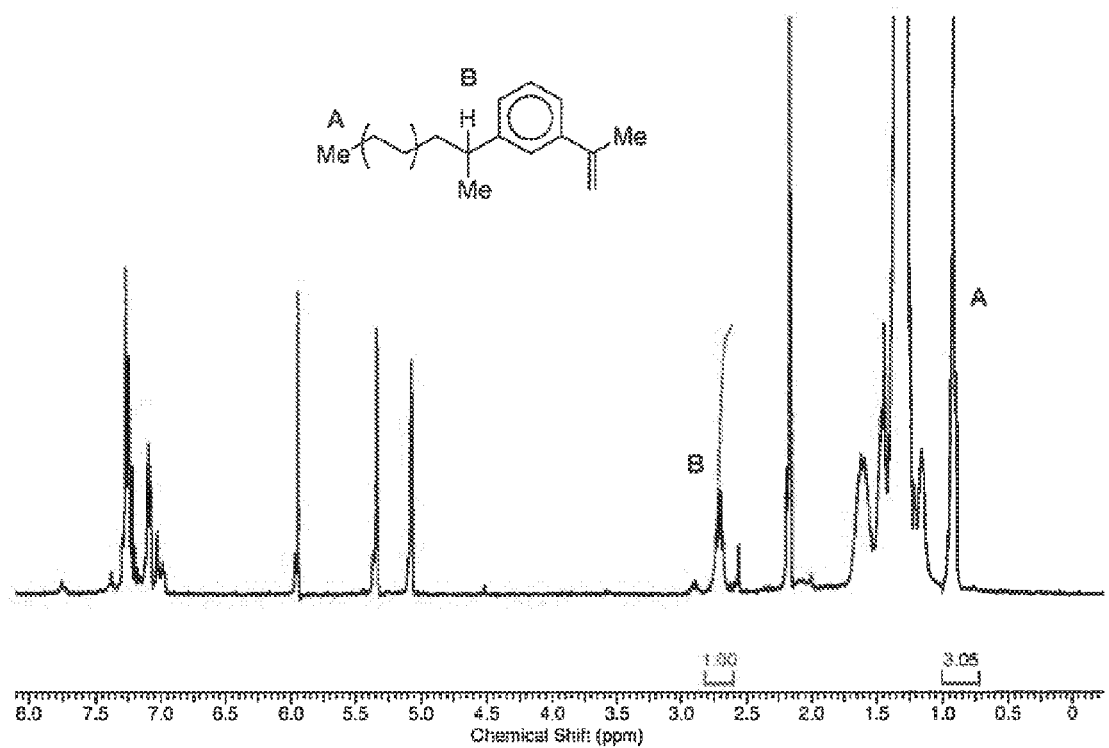

ADDITIVES FOR FUELS AND OILS COMPRISING FUNCTIONALISED DIBLOCK COPOLYMERS

CROSS-REFERENCE TO RELATED APPLICATIONS

This application is a DIV of Ser. No. 13/936,539, filed Jul. 8, 2013, now U.S. Pat. No. 9,540,583.

The present invention concerns performance-enhancing additives for fuels and oils, the additives comprising functionalised diblock copolymers having specific structures, together with a process for making such copolymers and other aspects of the invention as hereinafter described.

Base fuels and oils, i.e. the fuels and oils produced by processing of crude oil or other liquid or gaseous petroleum feedstocks, or by processing of biologically-derived material such as vegetable or animal oils and fats, or by synthetic means, are the basis for modern finished commercial fuels and oils, but by themselves typically lack the combination of specific properties for a specific application that is demanded by modern standards, legislation and/or consumer requirements. It has become commonplace in industry to enhance the properties of base fuels and oils by treatment with additives augmenting the relevant properties, so that they meet all the needs of the application in question.

In particular, many base fuels and oils naturally contain, as elements of their complex mixed compositions, one or more n-alkyl-, iso-alkyl- or n-alkenyl-substituted compounds, especially one or more n-alkanes, exhibiting a tendency to crystallise from the base fuel or oil in cold storage or use, thereby adversely affecting the cold flow behaviour of the base fuel or oil. As a result, transportation of the fuel or oil through the often complex distribution and vehicle systems for such products becomes problematic. Such problems include reduced flow and the blockage of filters, or even blockage of pipes where the crystallisation is so extensive that gelling of the fuel or oil occurs. In oils, as well as filter blockages, these gels can also create "channelling" of the oil where oil is drawn off initially, but the yield stress is high enough to leave most of the oil in the sump, leading to air being channelled and the vehicle failing by "air binding" of the pump. There is an ongoing need for solutions to this problem, and additives play an important role in improving the cold flow properties of such fluids, particularly in colder regions of the world where storage or use at cold ambient temperatures may be required for substantial periods.

A number of solutions have been proposed over the years to improve cold flow properties of fuels and oils, and commercial additives used today typically include various low molecular-weight ethylene-vinyl ester copolymers. Such copolymers tend to have random copolymeric structures, and are often used in blended mixtures to meet particular target performance needs.

On occasions, block copolymers wherein the blocks have been separately polymerised and then joined by coupling reactions between heteroatomic functional groups have been postulated. Such heteroatomic couplings are however open to cleavage by hydrolysis or other reactions, leading to degradation of the copolymer and loss of function.

Over time various other additive solutions have been proposed to improving the cold flow properties of fuels and oils, and these include wax anti-settling additives that typically comprise monomeric (rather than polymeric) compounds that serve to keep crystallised material better dispersed in the fuel. A variety of other monomeric or polymeric solutions have also been proposed.

Historically, the blend recipes of the base fuels or oils have sometimes been altered to incorporate more of the lower fuel or oil fractions in order to dilute the problematic compounds and provide a lighter base material with lower tendency towards cold flow problems. However, such an approach frequently suffers from adverse manufacturing economics from the viewpoint of refinery operations.

A need remains in the art for additives capable of effectively improving the cold flow properties of fuels and oils, and the present invention is particularly directed to the provision of new copolymeric materials having advantages as additives for this purpose.

The polymer art offers various types of copolymers. For example, previous work has demonstrated that, depending on the conditions, ethylene can be copolymerised with styrene and p-methylstyrene to form either copolymers in which the monomers are interspersed in the growing monomer chain, or materials having a polyethylene chain terminated with a single styrene or p-methylstyrene unit (for the latter, see the publication by J. Y. Dong and T. C. Chung entitled "Synthesis of Polyethylene Containing a Terminal p-Methylstyrene Group: Metallocene-Mediated Ethylene Polymerisation with a Consecutive Chain Transfer Reaction to p-Methylstyrene and a Hydrogen", reported in Macromolecules 2002, 35, 1622-1631). In particular, in the latter reference Chung et al. suggest the preparation of polyethylene which is substantially terminally functionalised by the addition of a single unit of styrene or p-methylstyrene via a proposed chain-transfer reaction, effected by certain metallocene catalysts in the presence of hydrogen. The resulting materials are thereafter postulated to be suitable for subsequent reaction, for example by metallation of the methyl group of p-methylstyrene, to prepare diblock copolymers. No industrial applications for such materials are suggested. Furthermore, the molecular weights reported for the functionalised polyethylenes produced by Chung et al. are higher than those of polymers typically used for industrial applications such as additives for improving the cold flow properties of many oils, and much higher than those of polymers used for improving the cold flow properties of fuels, especially fuels such as middle distillate fuels like diesel fuel.

Chung et al. also do not describe the terminal chain-transfer reaction of polyethylene with co-monomers other than styrene or p-methylstyrene. Furthermore, they do not postulate the preparation of a polyethylene chain with a more reactive terminal group that is more easily processed into industrially-useful chemicals, and do not address how that goal might be achieved.

EP-A-0 522 729 concerns an ethylene polymer cross linking composition using an organic peroxide as a cross-linking agent and a second compound as cross linking auxiliary compound. The process necessarily proceeds via a radical mechanism and relies on the peroxide. The resulting product is extensively cross-linked, and no reactive intermediate can be isolated as it proceeds.

The present invention concerns additives which comprise new functionalised diblock copolymers of the structure hereinafter defined. The additives are useful in fuels and oils, in particular for improving the cold flow behaviour of a fuel or oil composition derived from one or more petroleum, biological or synthetic sources and containing one or more n-alkyl- or iso-alkyl or n-alkenyl-substituted compounds, especially one or more n-alkanes, exhibiting a tendency to crystallise from the base fuel or oil in cold storage or use and thereby adversely affecting the cold flow behaviour of the base fuel or oil.

As used in this specification, the term "n-alkyl, iso-alkyl or n-alkenyl substituted compounds" collectively includes those compounds which are n-alkanes, those compounds which are iso-alkanes, those compounds which are n-alkenes, and those compounds containing n-alkyl, iso-alkyl or n-alkenyl groups, which exhibit a tendency to crystallise from fuel or oil at low temperatures. N-alkanes and iso-alkanes and n-alkenes on the one hand, and other compounds bearing n-alkyl, iso-alkyl or n-alkenyl substituents on the other hand, are typically present within base to fuels and oils, although the relative proportions and distributions of individual compounds differ from source to source. However, the invention described herein is particularly effective in relation to fuels and oils containing one or more n-alkanes, especially one or more long chain n-alkanes such as those having at least 20 carbon atoms, preferably at least 24 carbon atoms, which show a particular tendency to crystallise from the fuel or oil at low temperatures. Most of these fuels or oils will contain a range of such molecules, typically containing from 10 to 30 carbon atoms, although wider and narrower ranges are commonly seen.

The present invention further concerns fuel and oil compositions comprising the additives of the invention, and a method of improving the cold flow behaviour of a fuel or oil composition. In addition, the present invention concerns the new functionalised diblock copolymers of the structure hereinafter defined, along with their use to improve the cold flow behaviour of a fuel or oil composition, a process for their manufacture and the associated novel chemical intermediates.

FIG. 1 is a typical $^1$H NMR spectrum of intermediate compound (II) as produced by the process of the invention, as hereinafter detailed.

In a first aspect therefore, the present invention provides an additive concentrate comprising a functionalised diblock copolymer in admixture with an organic liquid miscible with fuel or oil, the copolymer comprising 2 polymeric blocks wherein:
    (i) the first block consists of a chain of ethylenic structural units, optionally interrupted by one or more structural units derived from 1-alkene co-monomers higher than ethylene, and
    (ii) the second block comprises a chain of Structural units derived from one or more α,β-unsaturated monomers selected from styrene, substituted styrene, acrylate, methacrylate and diene compounds,
and wherein said first and second blocks of the copolymer are terminally joined by means of the following structural linkage:

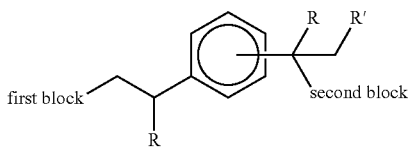

wherein each R group independently represents an alkyl or aryl group and R' represents hydrogen or an alkyl group, and wherein the aromatic ring substituent joined to the second block is positioned meta or para to the aromatic ring substituent joined to the first block.

In this specification, the word "terminal" when used in relation to a polymer chain (or block) simply refers to the end of the polymer chain (or block), and does not convey any additional mechanistic requirement that the chain (or block) end in question be the end at which the polymerisation reaction terminated. References to "terminally" shall be construed analogously.

In the structural formulae recited in this specification, it is also to be understood that any chiral centres are not intended to imply the selective formation or use of specific enantiomers; the materials of the invention should thus be taken to be racemic mixtures.

In a second aspect, the present invention provides a fuel or oil composition comprising:
    (i) a base fuel or oil derived from one or more petroleum, animal, vegetable or synthetic sources, the base fuel containing one or more n-alkyl-, iso-alkyl- or n-alkenyl-substituted compounds exhibiting a tendency to crystallise from the has fuel or oil in cold storage or use thereby adversely affecting the cold flow behaviour of the base fuel or oil, and
    (ii) the additive concentrate of the first aspect of the invention,
wherein the additive is present in the composition in an amount sufficient to improve the cold flow behaviour of the base fuel or oil during cold storage or use.

In a third aspect, the present invention concerns a method of improving the cold flow behaviour of a fuel or oil composition derived from one or more petroleum, animal, vegetable or synthetic sources and containing one or more n-alkyl-, iso-alkyl- or n-alkenyl-substituted compounds exhibiting a tendency to crystallise from the base fuel or oil in cold storage or use thereby adversely affecting the cold flow behaviour of the base fuel or oil, the method comprising:
    (i) determining the cold flow behaviour of the base fuel or oil in question and the improvement that is required;
    (ii) determining the amount of the additive concentrate of the first aspect necessary to effect the desired improvement in cold flow behaviour; and
    (iii) treating the base fuel or oil with that amount of the additive concentrate of the first aspect.

In this specification, the term "cold storage or use" of a fuel or oil refers to storage or use at temperatures below the Cloud Point of the fuel or oil, i.e. below the temperature at which, prior to treatment with the additive of the invention, the n-alkyl, iso-alkyl or n-alkenyl-substituted compounds present in that fuel or oil visibly begin to exhibit their tendency to crystallise from the fuel or oil. The Cloud Point is a well-known industry test, so-named because it observes the point at which the previously-clear fuel becomes 'cloudy' as fine crystals begin to visibly form from the bulk medium.

The advantageous properties of the additive concentrate are attributed to the nature of the diblock copolymer defined therein. In particular, and without being bound to any particular theory, it is believed that when present in the fuel or oil under cold storage or use conditions the polyethylenic chain of the first block of a copolymer molecule interacts with the growing crystal of n-alkyl-, iso-alkyl- or n-alkenyl-substituted compounds (and particularly n-alkane compounds) as they crystallise from the cold fuel or oil, thereafter inhibiting further crystal growth. This interaction is enabled by the geometry of polyethylenic sequences of the first block aligning with segments of the n-alkyl, iso-alkyl or n-alkenyl groups of the crystallising compounds. The second block of the polymer provides the correct dispersibility within the fuel, and provides steric hindrance to aid the blocking of further crystallisation at crystal growth sites.

In a fourth aspect, the invention is the functionalised diblock copolymer defined under any of the other aspects of the invention.

It is essential for the efficacy of the additive that the first block of the copolymer has a backbone chain of polyethylenic structural units. Interrupting this chain of the first polymer block with other structural units, such as an aromatic ring, which introduce a backbone segment that does not approximate in geometry to polyethylenic structural units, is unfavourable for performance in this application and is not part of the invention. However, it is permissible to incorporate in the backbone chain of the first block a proportion of co-monomer units derived from 1-alkenes higher than ethylene, such that the resulting polymer chain remains an uninterrupted is sequence of saturated aliphatic carbon atoms, the residual alkyl groups of the 1-alkene residues being borne as saturated alkyl substituents pendant from the polymer chain.

It is likewise important that the first block of the copolymer be terminally joined to the second block, so as to leave the first block exposed for interacting with the growing crystals in the fuel or oil. As such, it is important that the linkage between the first and second blocks be positioned at the end of the polymeric chain of the first block.

To achieve this terminal positioning of the linkage between the first and second blocks, it is essential that the process by which the copolymer is made be specific for terminal functionalization of the first block. Equally, it is important that the terminal functionalization formed on the first block be sufficiently reactive to enable the subsequent formation of the second block under process conditions that are industrially practical, whilst at the same time not being so highly reactive that unwanted side reactions occur to a significant extent.

The applicants have now found that, in the presence of hydrogen, a metallocene-catalysed polymerisation reaction between ethylene (and optionally higher 1-alkenes) and a compound of the formula (I):

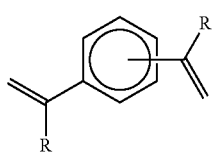

(I)

wherein each R group independently represents an alkyl or aryl group, and wherein the two aromatic ring substituents are positioned meta or para to each other, results in a highly specific reaction product being a terminally unsaturated intermediate compound of the formula (II):

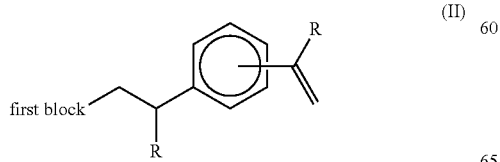

(II)

wherein R is as defined above in relation to compound (I).

The applicants have found that compound (II) is, by virtue of its terminal unsaturation, reactive towards subsequent reaction steps, in particular the polymerisation of the second block, and thus provides an industrially-useful starting point for further reaction. In particular, it is more usefully reactive than a pendant alkyl group towards metallation and subsequent anionic polymerisation. However, surprisingly, the applicants have also found that despite this terminal unsaturation, the compound (II) is stable and can be isolated; and is also not prone to significant spontaneous side reactions during its formation.

In particular, the applicants have found that despite compound (I) being di-unsaturated, it is not prone to multiple reaction with the growing polyethylene chains and does not give rise to appreciable cross-linking, resulting in a high proportion of the desired compound (II) being formed. The applicants have also found that compound (I) is specific for terminal incorporation with the first block, and does not appreciably incorporate within the body of the growing polyethylenic chain. This lack of 'in-chain' (as opposed to terminal) incorporation is in contrast to the reported tendency of the otherwise analogous material di-vinylbenzene to also incorporate in-chain to an appreciable extent, under similar reaction conditions with propylene, as reported in Macromol. Rapid Commun. 2005, 26, 1936-1941.

With the benefit of knowledge of this aspect of the invention, the applicants attribute this difference in specificity for terminal reaction to the presence of the R substituents on the vinyl groups of compound (I), which appear to distinguish its reactivity from di-vinylbenzene under such conditions. As a result, the compound (I) provides a favourable balance of reactivities to enable the preparation of the intermediate (II) and the subsequent copolymer.

The R substituents originating from compound (I) carry through as structural features into the intermediate (II) and thereafter, including further intermediates in the later processing and into the final copolymer. Thus, whilst the presence of the R substituents on the vinyl groups of compound (I) first appears to specify a single, terminal insertion into the polyethylene chain, the presence of the R substituent the remaining vinyl group in compound (II) also serves to moderate the reactivity of compound (II), and favourably direct the subsequent polymerisation reaction, particularly when this occurs through anionic polymerisation, where the R group serves to create a stable tertiary carbanionic centre during the metallation step. In the resulting block copolymer, the structure linking the first and second blocks is exclusively hydrocarbon in nature, and therefore not susceptible to hydrolysis or other cleavage reactions that may affect linkages comprised of heteroatomic functional groups such as ester or amides.

In a fifth aspect therefore, the invention is a process for manufacture of a functionalised diblock copolymer comprising 2 polymeric blocks wherein:
(i) the first block consists of a chain of ethylenic structural units, optionally interrupted by one or more structural units derived from 1-alkene co-monomer(s) higher than ethylene, and
(ii) the second block comprises a chain of structural units derived from one or more α,β-unsaturated monomers selected from styrene, substituted styrene, acrylate, methacrylate or diene compounds, and wherein said first and second blocks of the copolymer are terminally joined by means of the following structural linkage:

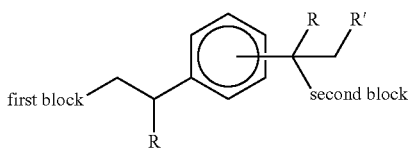

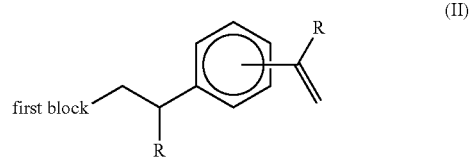

wherein each R group independently represents an alkyl or aryl group and R' represents hydrogen or an alkyl group, and wherein the aromatic ring substituent joined to the second block is positioned meta or para to the aromatic ring substituent joined to the first block;

the process comprising the following steps:

a) in a first step, polymerising ethylene, and optionally one or more alkene co-monomers higher than ethylene, in the presence of a metallocene catalyst system to form a first polymer block, being a chain consisting of ethylenic structural units optionally bearing pendent alkyl groups originating from 1-alkene comonomer(s), the reaction being carried out in solution at a temperature of at least 50° C. in the presence of a compound of the formula (I):

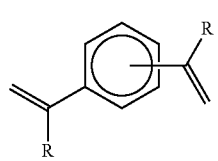

in a reaction vessel pressurised with hydrogen gas, wherein, in the course of the reaction, the compound (I) is terminally incorporated onto the first polymer block resulting in the formation of a terminally unsaturated intermediate of the formula (II):

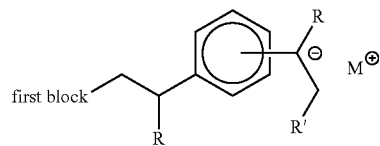

b) in a second step, recovering the intermediate (II) from the reaction mixture of the first step; and c) in a third step, reacting the intermediate (II) at its terminal double bond in a subsequent polymerisation reaction to form a second polymer block, so yielding a diblock polymer of the structure defined above.

In the process aspect of the invention, step c) is preferably an anionic polymerisation reaction, wherein the terminal double bond of the intermediate of formula (II) is reacted with a metallating reagent to form an anion which initiates polymerisation therefrom upon the addition of one or more α,β-unsaturated monomers selected from styrene, substituted styrene, acrylate, methacrylate and diene compounds.

In a sixth aspect, the invention is the isolated intermediate compound of the formula (II):

wherein each R group independently represents an alkyl or aryl group and R' represents hydrogen or an alkyl group, and wherein the aromatic ring substituent $C(R)=CH_2$ is positioned meta or para to the aromatic ring substituent joined to the first block.

The third step c) of the process of the fifth aspect is preferably an anionic polymerisation reaction, wherein the terminal double bond of the intermediate of formula (II) is reacted with a metallating reagent to form an anion which initiates polymerisation therefrom upon the addition of one or more α,β-unsaturated monomers selected from styrene, substituted styrene, acrylate, methacrylate and diene compounds.

This preferred aspect of the process proceeds via the conversion of the intermediate of the compound (II) into an anionic intermediate. Thus, in a seventh aspect, the invention is the anionic intermediate of the formula (III):

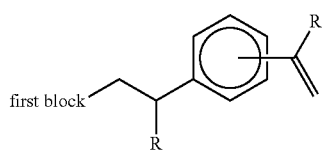

wherein each R group independently represents an alkyl or aryl group and wherein the aromatic ring substituent $—C^{(-)}(R)—CH_2(R')$ is positioned meta or para to the aromatic ring substituent joined to the first block; wherein R' represents an alkyl group and $M^+$ represents a metal cation, and $C^{(-)}$ represents a metallated carbanionic site.

In the fifth aspect, the metallating reagent is preferably an alkyl lithium more preferably n-butyl lithium, and in the seventh aspect, $M^+$ preferably represents a lithium cation.

In a final aspect, the invention concerns the use of the additive concentrate, and the use of the functionalised diblock copolymers defined therein, to improve the cold flow behaviour of a fuel or oil composition comprising a base fuel or oil derived from one or more petroleum, animal, vegetable or synthetic sources, the base fuel containing one or more n-alkyl-, iso-alkyl- or n-alkenyl-substituted compounds, and particularly one or more n-alkanes as hereinafter described, exhibiting a tendency to crystallise from the base fuel or oil in cold storage or use thereby adversely affecting the cold flow behaviour of the base fuel or oil.

The invention will now be described in more detail as follows.

The Additive Concentrate of the First Aspect

In accordance with the first aspect, the present invention provides an additive concentrate comprising the functionalized diblock copolymer defined herein in admixture with an organic liquid miscible in fuel or oil. The term 'in admixture with' as used herein means that the copolymer and organic liquid have been physically mixed together to provide a solution or dispersion of the polymer in the organic liquid, the latter functioning as a solvent or dispersing medium for the copolymer. Such liquids are sometimes collectively termed 'carrier fluids' in the art and assist the dispersion or dissolution of the additives they contain or oil, when the additive concentrate is blended into the base fuel or oil. Examples of suitable liquids include hydrocarbon solvents such as naphtha, kerosene, diesel and heater oil, aromatic hydrocarbons such as those sold under the 'SOLVESSO' trade name, alcohols, ethers and other oxygenates and paraffinic hydrocarbons such as hexane, pentane and isoparaffins. Likewise, the term 'miscible' as used herein means capable of being physically mixed with fuel or oil to form either a solution or a dispersion in the fuel or oil. The liquid is chosen having regard to its compatibility with both the polymer and the fuel or oil in question, and is a matter of routine choice for one skilled in the art. The additive concentrate may suitably comprise 1 to 95% by weight of organic liquid, preferably 10 to 70%, for example 25 to 60%, the remainder being the essential copolymer and any additional additives required to fulfill different purposes within the fuel or oil.

The essential functionalized diblock copolymer of the first aspect of the invention comprises 2 polymeric blocks wherein:
(i) the first block consists of a chain of ethylenic structural units, optionally interrupted by one or more structural units derived from 1-alkene co-monomers higher than ethylene, and
(ii) the second block comprises a chain of structural units derived from one or more α,β-unsaturated monomers selected from styrene, substituted styrene, acrylate, methacrylate and diene compounds, and wherein said first and second blocks of the copolymer are terminally joined by means of the following structural linkage:

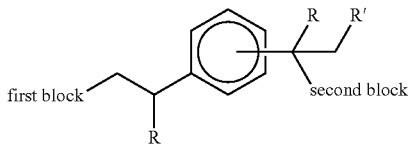

wherein each R group independently represents an alkyl or aryl group and the R' group represents hydrogen or an alkyl group, and wherein the aromatic ring substituent joined to the second block is positioned meta or para to the aromatic ring substituent joined to the first block. It is preferred that R' represents an alkyl group.

Preferably, in the additive concentrate the first and second blocks of the copolymer are terminally joined by means of the structural linkage:

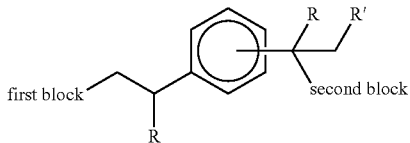

wherein each R group independently represents an alkyl group having from 1 to 4 carbon atoms and R' represents an alkyl group having from 1 to 10 carbon atoms.

More preferably, in the additive concentrate, the first and second blocks of the copolymer are terminally joined by means of the structural linkage:

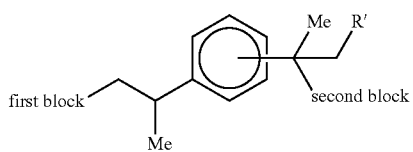

wherein R' represents an alkyl group having from 1 to 4 carbon atoms. More preferably, in the additive concentrate, R' represents a butyl group and most preferably an n-butyl group.

In the additive concentrate of the first aspect, it is particularly preferred that, in the copolymer, the aromatic ring substituent joined to the second block is positioned meta to the aromatic ring substituent joined to the first block.

In the additive concentrate of the first aspect, in order to function most effectively in the fuel or oil, it is particularly preferred that the first block of the copolymer consists of a polyethylene chain.

In one preferred embodiment, the second block of the copolymer consists of a chain of structural units derived from one or more α,β-unsaturated monomers selected from styrene, substituted styrene, acrylate and methacrylate compounds, More preferably, the second block of the copolymer consists of a homo- or copolymeric chain derived from one or more acrylate or methacrylate monomers. In particular, the (meth)acrylate monomer or monomers selected for the second block usefully comprise one or more (meth)acrylate compounds bearing a $C_4$-$C_{22}$ alkyl substituent, which may be branched or straight chain alkyl. Preferably the second block consists of a homo- or polymeric chain derived from one or more such monomers. Examples of such monomers are: 2-ethyl hexyl (meth)acrylate, isodecyl (meth)acrylate, t-butyl (meth)acrylate, dodecyl (meth)acrylate, decyl(meth) acrylate, and those with a $C_{12}$-$C_{15}$ chain length based on Neodol 25 from Shell.

The second block act, in part, as a solubilising and/or dispersing group for the copolymer.

In another preferred embodiment, the second block of the copolymer consists of a chain of structural units derived from one or more diene compounds. These dienes may be unhydrogenated, hydrogenated or partially hydrogenated dienes. More preferably, the second block of the copolymer consists of a homo- or copolymeric chain derived from isoprene or butadiene or a mixture thereof.

In the additive concentrate of first aspect of the invention, the first block of the copolymer preferably has a number average molecular weight (Mn), as measured by GPC against polystyrene standards, in the range of 500 to 20,000 g mol$^{-1}$. For optimum performance in fuel, it is preferred that the Mn of the first block of the copolymer be in the range of 500 to 10,000 g mol$^{-1}$, more preferably 500 to 5,000 g mol$^{-1}$.

The Fuel Oil Composition of the Second Aspect

The second aspect of the invention is a fuel or oil composition comprising:
(i) a base fuel or oil derived from one or more petroleum, animal, vegetable or synthetic sources, the base fuel containing one or more n-alkyl-, iso-alkyl or n-alkenyl-substituted compounds exhibiting a tendency to crystallise from the base fuel or oil in cold storage or use thereby adversely affecting the cold flow behaviour of the base fuel or oil, and (ii) the additive concentrate of the first aspect, wherein the additive is present in the composition in an amount sufficient to improve the cold flow behaviour of the base fuel or oil during cold storage or use.

The base fuel may be a petroleum-based fuel oil, especially a middle distillate fuel oil. Such distillate fuel oils generally boil within the range of from 110° C. to 500° C., e.g. 150° C. to 400° C. The invention is applicable to middle distillate fuel oils of all types, including the distillates having a 90%-20% boiling temperature difference, as measured in accordance with ASTM D-86, of 50° C. or more.

The base fuel may comprise atmospheric distillate or vacuum distillate, cracked gas oil, or a blend in any proportion of straight run and thermally and/or catalytically cracked distillates. The most common petroleum distillate fuels are kerosene, jet fuels, diesel fuels, heating oils and heavy fuel oils. The heating oil may be a straight atmospheric distillate, or may also contain vacuum gas oil or cracked gas oil or both. The fuels may also contain major or minor amounts of components derived from the Fischer-Tropsch process. Fischer-Tropsch fuels, also known as FT fuels, include those that are described as gas-to-liquid fuels, coal and/or biomass conversion fuels. To make such fuels, syngas ($CO+H_2$) is first generated and then converted to normal paraffins and olefins by a Fischer-Tropsch process. The normal paraffins may then be modified by processes such as catalytic cracking/reforming or isomerisation, hydrocracking and hydroisomerisation to yield a variety of hydrocarbons such as iso-paraffins, cyclo-paraffins and aromatic compounds. The resulting FT fuel can be used as such or in combination with other fuel components and fuel types such as those mentioned in this specification.

The second aspect of the invention is also applicable to base fuels containing fatty acid alkyl esters made from oils derived from animal or vegetable materials, often called biofuels or biodiesels. Biofuels are believed by some to be less damaging to the environment on combustion and are obtained from a renewable source. Other forms of biofuels are also included in the invention such as hydrogenated vegetable oil (HVO) and oil derived from alternative sources such as algae.

Examples of base fuels derived from animal or vegetable material are rapeseed oil, canola oil, coriander oil, soyabean oil, cottonseed oil, sunflower oil, castor oil, olive oil, peanut oil, maize oil, almond oil, palm kernel oil, coconut oil, mustard seed oil, jatropha oil, beef tallow and fish oils. Further examples include fuel oils derived from corn, jute, sesame, shea nut, ground nut and linseed oil and may be derived therefrom by methods known in the art. Rapeseed oil, which is a mixture of fatty acids partially esterified with glycerol is available in large quantities and can be obtained in a simple way by pressing from rapeseed. Recycled oils such as used kitchen oils are also suitable.

As alkyl esters of fatty acids, consideration may be given to the following, for example as commercial mixtures the ethyl, propyl, butyl and especially methyl esters of fatty acids with 12 to 22 carbon atoms, for example of lauric acid, myristic acid, palmitic acid, palmitoleic acid, stearic acid, oleic acid, elaidic acid, petroselic acid, ricinoleic acid, elaeostearic acid, linoleic acid, linolenic acid, eicosanoic acid, gadoleic acid, docosanoic acid or erucic acid, which have an iodine number from 50 to 150, especially 90 to 125. Mixtures with particularly advantageous properties are those which contain mainly, i.e. to at least 50 wt % methyl esters of fatty acids with 16 to 22 carbon atoms and 1, 2 or 3 double bonds. The preferred alkyl esters of fatty acids are the methyl esters of oleic acid, linoleic acid, linolenic acid and erucic acid.

Commercial mixtures of the stated kind are obtained for example by cleavage and esterification of animal and vegetable fats and oils by their transesterification with lower (ca. $C_1$ to $C_6$) aliphatic alcohols. For production of alkyl esters of fatty acids it is advantageous to start from fats and oils which contain low levels of saturated acids, less than 20%, and which have an iodine number of less than 130. Blends of the following esters or oils are suitable, e.g. rapeseed, sunflower, canola, coriander, castor, soyabean, peanut, cotton seed, beef tallow etc. Alkyl esters of fatty acids based on certain varieties of rapeseed oil having more than 80 wt % of unsaturated fatty acids with 18 carbon atoms, are particularly suitable.

Whilst all of the above biofuels may be used as base fuels, preferred are vegetable oil derivatives, of which particularly preferred biofuels are alkyl ester derivatives of rapeseed oil, cottonseed oil, soyabean oil, sunflower oil, olive oil, or palm oil, rapeseed oil methyl ester being especially preferred. Such fatty acid methyl esters are often referred to in the art as FAME.

The invention is also applicable to pure biofuels. In one embodiment therefore, the base fuel comprises essentially 100% by weight of a fuel derived from a plant or animal source, preferably essentially 100% by weight of fatty acid alkyl esters, most preferably fatty acid methyl esters.

Biofuels are commonly used in combination with petroleum-derived base fuels. The present invention is also applicable to mixtures of biofuel and petroleum-derived base fuels in any ratio. Such fuels are often termed "Bx" fuels where x represents the percentage by weight of biofuel in the biofuel-petroleum blend. Examples, include fuels where x is 2 or above, preferably 5 or above, for example up to 10, 25, 50, or 95. Preferably the biofuel component in such Bx base fuels comprises fatty acid alkyl esters, most preferably fatty acid methyl esters.

The base fuel, whether petroleum or vegetable or animal-derived, or synthetic, preferably has a low sulphur content. Typically, the sulphur content of the fuel will be less than 500 ppm (parts per million by weight). Preferably, the sulphur content of the fuel will be less than 100 ppm, for example, less than 50 ppm. Fuels with even lower sulphur contents, for example less that 20 ppm or less than 10 ppm are also suitable.

Base oils useful in the context of the present invention include those oils of lubricating viscosity, preferably selected from natural lubricating oils, synthetic lubricating oils and mixtures thereof. The base oil may range in viscosity from light distillate mineral oils to heavy lubricating oils such as gasoline engine oils, mineral lubricating oils and heavy duty diesel oils, and marine lubricants. Generally, the viscosity of the base oil ranges from about 2 centistokes to about 40 centistokes, especially from about 4 centistokes to about 20 centistokes, as measured at 100° C.

Natural base oils include animal oils and vegetable oils (e.g., castor oil, lard oil); liquid petroleum oils and hydrorefined, solvent-treated or acid-treated mineral oils of the paraffinic, naphthenic and mixed paraffinic-naphthenic types. Base oils of lubricating viscosity derived from coal or shale also serve as useful base oils.

Synthetic base lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and derivative, analogs and homologs thereof. Also useful are synthetic oils derived from a gas to liquid process from Fischer-Tropsch synthesized hydrocarbons, which are commonly referred to as gas to liquid, or "GTL" base oils.

Alkylene oxide polymers and interpolymers and derivatives thereof where the terminal hydroxyl groups have been modified by esterification, etherification, etc., constitute another class of known synthetic base oils. These are exemplified by polyoxyalkylene polymers prepared by polymerization of ethylene oxide or propylene oxide, and the alkyl and aryl ethers of polyoxyalkylene polymers (e.g., methylpolyiso-propylene glycol ether having a molecular weight of 1000 or diphenyl ether of poly-ethylene glycol having a molecular weight of 1000 to 1500); and mono- and polycarboxylic esters thereof, for example, the acetic acid esters, mixed $C_3$-$C_8$ fatty add esters and $C_{13}$ oxo acid diester of tetraethylene glycol.

Another suitable class of synthetic base oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, is adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of such esters includes dibutyl adipate, di(2-ethylhexyl) sebacate, di-n-hexyl fumarate, dioctyl sebacate, diisooctyl azelate, diisodecyl azelate, dioctyl phthalate, didecyl phthalate, dicicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic base oils also include those made from $C_5$ to $C_{12}$ monocarboxylic acids and polyols and polyol esters such as neopentyl trimethylolpropane, pentaerythritol, dipentaerythritol and tripentaerythritol, Silicon-based base oils such as the polyalkyl-, polyaryl-, polyalkoxy- or polyaryloxysilicone oils and silicate oils comprise another useful class of synthetic lubricants; such oils include tetraethyl silicate, tetraisopropyl silicate, tetra-(2-ethylhexyl)silicate, tetra-(4-methyl-2-ethylhexyl)silicate, tetra-(p-tert-butyl-phenyl) 3D silicate, hexa-(4-methyl-2-ethylhexyl)disiloxane, poly(methyl)siloxanes and poly(methylphenyl)siloxanes. Other synthetic lubricating oils include liquid esters of phosphorous-containing acids (e.g., tricresyl phosphate, trioctyl phosphate, diethyl ester of decylphosphonic acid) and polymeric tetrahydrofurans.

Base oils of lubricating viscosity may comprise a Group I, Group II or Group III, base stock or base oil blends of the aforementioned base stocks. Preferably, the oil is of lubricating viscosity and is a Group II or Group III base stock, or a mixture thereof, or a mixture of a Group I base stock and one or more a Group II and Group III. Preferably, a major amount of the oil of lubricating viscosity is a Group II, Group III, Group IV or Group V base stock, or a mixture thereof. The base stock, or base stock blend preferably has a saturate content of at least 65%, more preferably at least 75%, such as at least 85%. Most preferably, the base stock, or base stock blend, has a saturate content of greater than 90%. Preferably, the base oil or oil blend will have a sulfur content of less than 1%, preferably less than 0.6%, most preferably less than 0.4%, by weight. Equally, the base oil or base oil blend may be hydrodesulphurised to sulphur content of very low levels, typically 1500 ppm by weight or less, preferably 15 ppm by weight or less.

Preferably the volatility of the base oil or oil blend, as measured by the Noack volatility test (ASTM D5880), is less than or equal to 30%, preferably less than or equal to 25%, more preferably less than or equal to 20%, most preferably less than or equal 16%. Preferably, the viscosity index (VI) of the oil or oil blend is at least 85, preferably at least 100, most preferably from about 105 to 140.

Definitions for the base stocks and base oils suitable for use in this invention are the same as those found in the American Petroleum Institute (API) publication "Engine Oil Licensing and Certification System", Industry Services Department, Fourteenth Edition, December 1996, Addendum 1, December 1998. Said publication categorizes base stocks as follows:

a) Group I base stocks contain less than 90 percent saturates and/or greater than 0.03 percent sulfur and have a viscosity index greater than or equal to 80 and less than 120 using the test methods specified in Table 1.
b) Group II base stocks contain greater than or equal to 90 percent saturates and less than or equal to 0.03 percent sulfur and have a viscosity index greater than or equal to 80 and less than 120 using the test methods specified in Table 1.
c) Group III base stocks contain greater than or equal to 90 percent saturates and less than or equal to 0.03 percent sulfur and have a viscosity index greater than or equal to 120 using the test methods specified in Table 1.
d) Group IV base stocks are polyalphaolefins (PAO).
e) Group V base stocks include all other base stocks not included in Group I, II, III, or IV.

The additive concentrate of the first aspect is added to the base fuel or oil in an amount sufficient to improve the cold flow behaviour of the base fuel or oil during cold storage or use. In practice, the resulting amount of essential copolymer present in the base fuel or oil in question may vary with the type of fuel or oil, and the cold flow behavior desired, and will be determined by the individual circumstances and needs.

Suitably however, the additive concentrate will be added to base fuels in such an amount that it provides the essential copolymer in an amount of between 10 and 5,000, preferably between 10 and 1,000, more preferably between 50 and 500 ppm by weight, based on the weight of the fuel.

Also suitably the additive concentrate will be added to base oils in such an amount that it provides the essential copolymer in an amount of between 10 and 5,000 preferably between 10 and 1,000, more preferably between 50 and 500 ppm by weight, based on the weight of the oil.

With regard to the second aspect of the invention, improvement of the cold flow behaviour of a fuel or oil will be understood by those skilled in the art to refer to the ability of the fuel or oil to flow, to be pumped or to pass through filter media when cooled to low ambient temperatures such as may be experienced by vehicles operating in regions with cold climates. For example, tests such as the Cold Filter Plugging Point test (CFPP) and the Pour Point test (PP) are widely used in the industry to determine fuel and/or oil operability at low temperatures. These tests are designed to determine filterability and/or flowability at temperatures wherein the tendency towards crystallization of n-alkyl, iso-alkyl or n-alkenyl substituted compounds, and particularly n-alkanes, is exhibited. Improvements in this cold flow behavior due to the presence of the additive of the invention can be readily determined by comparative tests of the fuel with or without the additive in question.

However, the present invention in all its aspects is particularly applicable to those base fuels or oils that contain one or more n-alkanes or n-alkenes, preferably one or more n-alkanes, in particular one or more alkanes containing at least 20 carbon atoms, and more preferably one or more alkanes containing at least 24 carbon atoms, such as at least 26, 27, 28, 29 or 30 carbon atoms. Such compounds exhibit a well-known tendency to crystallise from the base fuel or oil in cold storage or use, thereby adversely affecting the cold flow behaviour of the base fuel or oil. Base fuels and oils containing such compounds thus particularly suffer from the problem addressed by this invention and are particularly suitable to treatment from the additive described herein, and compositions containing such base fuels are particularly preferred under the second aspect of the invention.

More preferably, these preferred compositions of the second aspect comprise a base fuel which is a diesel fuel or heating oil, being either a petroleum-derived base fuel, or a mixture of petroleum-derived base fuel and vegetable-derived base fuel, or a vegetable-derived base fuel. Most preferably, the compositions of the second aspect comprise a base fuel which is a diesel fuel being either a petroleum-derived base fuel, or a mixture of petroleum-derived base fuel and vegetable-derived base fuel, containing one or more n-alkanes containing at least 20 carbon atoms, and more preferably containing at least 25 carbon atoms, such as at least 26, 27, 28, 29 or 30 carbon atoms.

The Method of the Third Aspect

The third aspect of the invention provides a method of improving the cold flow behaviour of a fuel or oil composition derived from one or more petroleum, animal, vegetable or synthetic sources and containing one or more n-alkyl- or iso-alkyl or n-alkenyl-substituted compounds exhibiting a tendency to crystallise from the base fuel or oil in cold storage or use thereby adversely affecting the cold flow behaviour of the base fuel or oil, the method comprising:
 (i) determining the cold flow behaviour of the base fuel or oil in question and the improvement that is required;
 (ii) determining the amount of the additive concentrate of the first aspect necessary to effect the desired improvement in cold flow behaviour; and
 (iii) treating the base fuel or oil with that amount of the additive concentrate.

In the method aspect of the invention, the base fuel and oil, and the additive concentrate, are those defined in relation to the first and second aspects above.

The method involves determining the necessary amount of additive for a given base fuel or oil in a given circumstance. In practice, the desired cold flow properties of a fuel or oil are usually specified by the fuel or oil manufacturer, in relation to desired performance in the industry test(s) adopted by that manufacturer as most relevant to the environment the fuel or oil is likely to meet. These performance targets, when compared to the performance of the base fuel alone, provide a clear target for the necessary improvement which the additive must achieve in a given case. It is a matter of normal skill in the art to thereafter determine the amount of additive that must be used to achieve that desired improvement, through comparative experiments in those test(s) specified by the manufacturer.

The Funtionalised Diblock Copolymer of the Fourth Aspect

The preferred embodiments of the copolymer of the fourth aspect of the invention are those defined in relation to any of the other aspects of the invention. For brevity these are not reproduced verbatim.

The Process of the Fifth Aspect

The fifth aspect of the invention is a process for manufacture of a functionalised diblock copolymer comprising 2 polymeric blocks wherein:
 (i) the first block consists of a chain of ethylenic structural units, optionally interrupted by one or more structural units derived from 1-alkene co-monomers higher than ethylene, and
 (ii) the second block comprises a chain of structural units derived from one or more α,β-unsaturated monomers selected from styrene, substituted styrene, acrylate, methacrylate and diene compounds,
and wherein said first and second blocks of the copolymer are terminally joined by means of the following structural linkage:

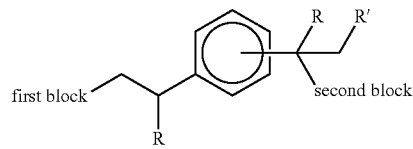

wherein each R group independently represents an alkyl or aryl group and R' represents hydrogen or an alkyl group, and wherein the aromatic ring substituent joined to the second block is positioned meta or para to the aromatic ring substituent joined to the first block;

the process comprising the following steps:
 a) in a first step, polymerising ethylene, and optionally one or more 1-alkene co-monomers higher than ethylene, in the presence of a metallocene catalyst system to form a first polymer block, being a chain consisting of ethylenic structural units optionally bearing pendent alkyl groups originating from 1-alkene comonomer(s), the reaction being carried out in solution at a temperature of at least 50° C. in the presence of a compound of the formula (I):

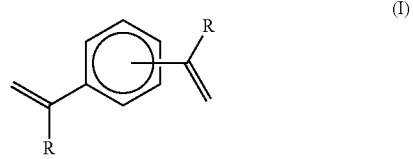

in a reaction vessel pressurised with hydrogen gas,
wherein, in the course of the reaction, the compound (I) is terminally incorporated onto the first polymer block resulting in the formation of a terminally unsaturated intermediate of the formula (II):

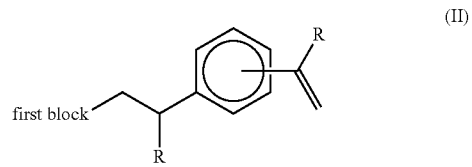

b) in a second step, recovering the intermediate (II) from the reaction mixture of the first step; and c) in a third step, reacting the intermediate (II) at its terminal double bond in a subsequent polymerisation reaction to form a second polymer block, so yielding a diblock polymer of the structure defined above.

In the process aspect of the invention, step c) is preferably an anionic polymerisation reaction, wherein the terminal double bond of the intermediate of formula (II) is reacted with a metallating reagent to form an anion which initiates polymerisation therefrom upon the addition of one or more α,β-unsaturated monomers selected from styrene, substituted styrene, acrylate, methacrylate and diene compounds.

The preferred embodiments of the process of the fifth aspect of the invention are those giving rise to the preferred embodiments of the functionalised block copolymer defined in relation to the other aspects of the invention. For brevity these preferred polymers are not reproduced verbatim.

The first step a) of the process proceeds at a reaction medium temperature of at least 50° C., preferably at least 55° C., and more preferably at least 58'C, such as at least 60° C. This minimum temperature avoids compound (I) homopolymerising significantly in the presence of the metallocene catalyst, and thus avoids an unwanted competing reaction. Preferably, the reaction temperature is maintained within the range of 55° C. to 90° C., more preferably in the range of 58° C. to 80° C.

The first step a) of the process is also essentially conducted in a vessel under pressure in the presence of hydrogen gas. Hydrogen is required to enable the necessary reaction to take place between the growing polyethylenic chain, the metallocene catalyst and the compound (I), leading to the terminal insertion of the compound (I) on the polyethylenic chain. Maintaining the pressure of the system during this step is also important to obtaining good productivity in the reaction and effective molecular weight control of the first polymer block.

Preferably, the partial pressure of hydrogen in the reaction vessel is set to between 170 and 280 kPa, preferably in the range of 185 to 242 kPa. Also preferably, the partial pressure of ethylene in the reaction vessel is preferably set to between 35 and 440 kPa, more preferably in the range of 70 to 415 kPa, most preferably in the range of 80 to 285 kPa.

More preferably, the partial pressure of hydrogen in the reaction vessel is set to between 185 to 242 kPa and the partial pressure of ethylene is set to between 80 and 285 kPa.

Suitable metallocene catalysts comprise a Transition Metal, particularly a metal from group IV of the periodic table such as Ti, Zr or Hf, with one or more ligands such as cyclopentadienyl ("Cp"), substituted cyclopentadienyl (including indenyl, fluorenyl and their derivatives), and bridged variants of the above. Additional ligands may be coordinated or bonded to the metal by heteroatoms such as N, O, S or P and may include bridges to Cp-type ligands as above.

Such catalysts are normally synthesised and stored as a metal dichloride/dialkyl (e.g. dibenzyl) or mono-alkyl-mono-chloride species ("pre-catalyst"). This is activated in solution by addition of a co-catalyst, generally methylaluminoxane (MAO), but alternatively a combination of a boron containing species such as $Ph_3C+B(C_6F_5)_4-$ and a trialkylaluminium species such as $i-(C_4H_9)_3Al$. In practice, the choice of metallocene catalyst will be exercised by the skilled chemist in accordance with conventional principles. Amongst relevant principles, the essential presence of hydrogen in the reaction naturally dictates that the catalyst chosen should be one whose function is not impaired by hydrogen.

Examples of such catalysts include $C_2MCl_2$, $Cp^*_2MCl_2$, $Flu(Ph_2Me)CpMCl_2$, and $Cp(Me)_4(Me_2Si)NtBuMCl_2$, wherein M represents a transition metal, Most preferred catalysts are catalysts in which M represents zirconium. The most preferred catalyst is $Cp_2ZrCl_2$ and the most preferred co-catalyst is MAO.

The following is a working example of the first step of the process.

Working Example 1—Step a) of the Process Preparation of Compound (II)

A 250 ml stainless steel Parr reactor with internal cooling coil was dried under vacuum at 100° C. for 1 hour before addition of a comonomer solution consisting of toluene (50 ml), 1,3-diisopropenylbenzene (30 ml, 0.175 mol—compound (1)) and MAO solution (3 ml, 1800 equivalents) via cannula with the reactor initially heated to 50° C. The reactor was purged for 5 min with hydrogen (240 kPa) before the addition of ethylene (85 kPa). Once ethylene uptake had stabilised, a toluene solution of metallocene catalyst $Cp_2ZrCl_2$ ($2.5 \times 10^{-6}$ mol) prepared in the glovebox was injected using an overpressure of argon. After catalyst addition, the temperature and gas uptake were continuously monitored. The reaction temperature was maintained at 60° C. The reaction was stopped after 15 min by careful addition of methanol (2×10 ml). The polymer product was precipitated by pouring into a solution of 5% HCl in methanol (600 ml) with stirring for 1 h. The product was recovered by filtration and washed with methanol, and once dry washed again with tetrahydrofuran (200 ml). The polymer product, 1,3-diisopropenylbenzene terminated polyethylene (compound (II), being PE-t-DIB) was dried by heating to 70° C. in vacua for 24 h, giving a yield of 1655 g.

The productivity of the reaction was 4235 kg (Polymer)/(mol[cat.]h). The 1,3-DIB content of the resulting polymer (compound (II)) was 2.54 mol % and it had an Mw of 3269 g $mol^{-1}$, an $M_n$ of 1893 g $mol^{-1}$, and Dispersity (PDi) of 1.73, as measured by high temperature GPC was performed in 1,2,4-trichlorobenzene at 160° C. at a flow rate of 1 ml/min on a Polymer Labs PL220 fitted with a 5 cm PLgel guard column (5 μM), and two PLgel 30 cm Mixed-D columns (5 μM). Calibration was achieved using Polymer Labs PSM Ensivial polystyrene standards. The molecular weight is determined by comparing the retention time of the polymer with that of the calibration curve at that retention time.

The characterisation of compound II, to confirm the desired terminal functionalisation structure is obtained, can be conducted by nuclear magnetic resonance spectroscopy.

For example, NMR spectra can be recorded on Bruker DPX400 and DPX500 spectrometers, wherein $^1H$ and $^{13}C$ NMR spectra are referenced internally using the solvent resonances relative to tetramethylsilane. Routine NMR assignments (including polymer samples) can be confirmed by $^1H$-$^1H$ (COSY), $^{13}C$-$^1H$ (HMQC) and $^{13}C$-$^1H$ (HMBC) correlation experiments where necessary.

In particular, to confirm the terminal insertion of the compound (I), $^1H$ NMR spectroscopy can be employed. For example, shown in the attached FIG. 1 is a typical $^1H$ NMR spectra for a compound (II) as produced by the above process step a), employing ethylene as the constituent of the first polymer block, and 1,3-diisopropenylbenzene ("1,3-DIB") as compound I. Determination of the amount of terminal insertion is achieved by comparison of the spectroscopic peaks for a methyl group at one end of the polyethylene chain which has three protons (labelled A in the FIGURE), and a single proton on the benzylic carbon of the 1,3-DIB molecule remaining after step a) of the reaction (labelled B in the FIGURE). Any 1,3-DIB incorporated in-chain would not have a proton on this carbon, and thus this proton resonance serves to distinguish terminal insertion of the 1,3-DIB.

The $^1$H NMR peaks associated with these protons (A and B) have chemical shifts of 0.91 ppm and 2.71 ppm respectively (chemical shifts are measured against the residual solvent signal in d$_2$-TCE at 5.94 ppm). Comparing the integrals of these two peaks gives the amount of terminal insertion by 1,3-DIB. As can be seen for example in the spectrum shown, an integrals ratio of the respective peaks of 3:1 (A:B) indicates that essentially each polyethylene chain is terminally functionalised by the residue from the 1,3-DIB.

An advantage of the process of the invention is in securing a high degree of terminal functionalization of the first block, as determined by the above spectroscopic method. Thus, further examples of step a) of the process and the results achieved are shown below:

Further Worked Examples 2 to 5 of the Process Step a) and Compound (II)

Following the above worked example but with the process conditions in step a) adjusted as shown in the table below, further examples of compound (II) were conducted as follows:

| Example no | Co-monomer | Monomer | Hydrogen pressure (kPa) | Ethylene pressure (kPa) | Reaction Temperature (° C.) | Productivity (kg polymer/mol[M] h) |
|---|---|---|---|---|---|---|
| 2 | 1,3-DIB | ethylene | 240 | 285 | 62 | 13754 |
| 3 | 1,3-DIB | ethylene | 240 | 285 | 61 | 13758 |
| 4 | 1,3-DIB | ethylene | 240 | 285 | 63 | 13307 |

In each case, the reaction resulted in essentially complete terminal functionalization of the polyethylenic chains by co-monomer compound (I), so forming compound (II) to a highly specific degree. The high productivity achieved in the reaction is also shown in the table.

The compound II can be isolated as demonstrated in the worked example 1, or by other means of recovery known to the polymer chemist.

The preferred embodiments of the process, and of the resulting compound II, are those resulting from the preferred forms of compound (I) described above, and in particular from those preferred compounds in combination with a first block consisting of polyethylene.

Thus in the process and compound (II) aspects of the invention, the originating compound (I) preferably has the structure:

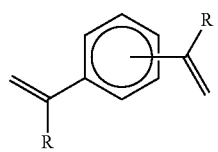

wherein each R group independently represents an alkyl group having from 1 to 4 carbon atoms.

More preferably, the originating compound (I) has the structure:

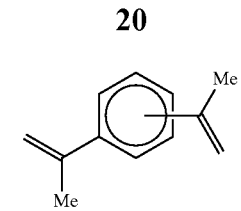

Most preferably, in the above preferred embodiments of compound (I), the aromatic ring substituents are positioned meta to each other.

The third step c) of the process of the invention involves the formation of the second block. Preferably, the third step c) is an anionic polymerisation reaction, wherein the terminal double bond of the compound of formula (II) is reacted with a metallating reagent to form an anion which initiates polymerisation therefrom upon the addition of one or more α,β-unsaturated monomers bearing one or more functional groups selected from styrene, substituted styrene, acrylate, methacrylate and diene compounds.

Preferably, in the anionic polymerisation, the metallating agent is an alkyl metal compound R'M and the compound (II) has the structure:

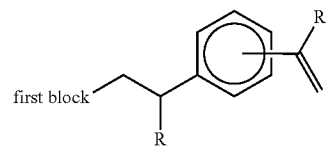

wherein each R group independently represents an alkyl group having from 1 to 4 carbon atoms; and wherein, in the course of the third reaction step c), the alkyl group R' of the alkyl metal compound inserts onto the less-substituted carbon of the double bond, giving rise to a reactive anionic intermediate having the structure of the formula (III):

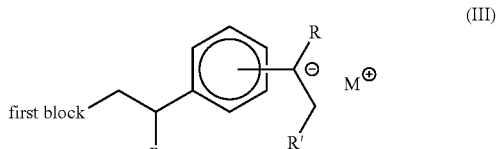

(III)

wherein R' represents the inserted alkyl group originating from the alkyl metal compound, $^{(-)}$ represents the metallated carbanionic site from which the anionic polymerisation of the third reaction step thereafter proceeds, and M$^{(+)}$ represents the metal cation originating from the metal M of the alkyl metal compound, In this process, the metallating reagent preferably comprises n-butyl lithium or sec-butyl lithium, such that $M^{(+)}$ in the above formula represents a lithium cation and R' represents n-butyl or sec-butyl.

Particularly preferred is a process wherein the compound (II) has the structure:

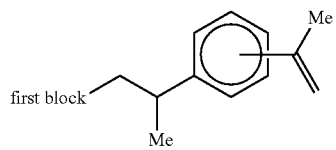

and the metallating reagent comprises n-butyl lithium.

Further embodiments of the invention include the isolated intermediate compound of the formula (II):

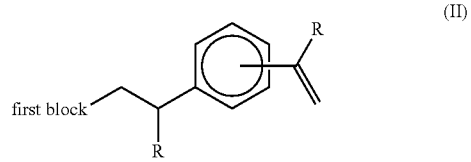

wherein each R group independently represents an alkyl or aryl group, and wherein the aromatic ring substituent C(R)=CH$_2$ is positioned meta or para to the substituent joined to the first block; and the anionic intermediate of the formula (III):

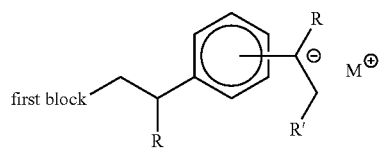

wherein each R group independently represents an alkyl or aryl group and wherein the aromatic ring substituent —C$^{(-)}$(R)—CH$_2$(R') is positioned meta or para to the aromatic ring substituent joined to the first block; wherein R' represents an alkyl group and M$^+$ represents a metal cation, and C$^{(-)}$ represents a metallated carbanionic site.

Preferably, in the compound (II) and the anionic intermediate each R group independently represents an alkyl group having from 1 to 4 carbon atoms. More preferably, each R group independently represents a methyl group. Also preferably, R' represents n-butyl, Most preferably, each R group independently represents a methyl group and R' represents n-butyl.

Equally, in compound (II) and the anionic intermediate it is preferred that the two aromatic ring substituents are positioned meta to each other.

In a preferred embodiment, compound (II) and the anionic intermediate have a first block having a number average molecular weight (Mn), as measured by GPC against polystyrene standards, in the range of 500 to 20,000 g mol$^{-1}$ and preferably in the range of 500 to 10,000 g mol$^{-1}$, more preferably 500 to 5,000 g mol$^{-1}$. More preferably, the first block consists of a polyethylene chain, Working Example 2—Step c) of the Process—Anionic Polymerisation In a typical anionic polymerisation example, a Schlenk vessel equipped with a stirrer bar was charged with 1,3-diisopropenylbenzene terminated polyethylene (compound (II), being PE-t-DIB) (0.5 g, 3.6×10$^{-4}$ mol) before cyclohexane (50 ml) and n-butyllithium solution (2 ml, 5×10$^{-3}$ mol) were added via cannula. The reaction mixture was stirred and heated to 70° C. using an aluminium heating block for 3 h. The reaction was allowed to cool and the thus lithiated polymer intermediate (red) was allowed to settle before a filter cannula was used to remove the solvent and excess n-butyllithium, The polymer intermediate was washed twice with cyclohexane (2×50 ml) and cyclohexane (50 ml) and styrene (2 ml, 1.7×10$^{-2}$ mol) added at ambient temperature with stirring. After 19 h the reaction was terminated by addition of methanol (10 ml) and the precipitated diblock copolymer was filtered and dried overnight in vacuo for 24 h. The yield was 2.692 g and the final polymer characterised as M$_W$ of 81877 g mol$^{-1}$, M$_n$ of 47440 g mol$^{-1}$, and a Dispersity of 1.73 as measured by the GPC method described previously in relation to the worked example of step a).

The effectiveness of the functionalised diblock copolymers described herein in improving the cold flow behaviour of fuels and oils is illustrated hereafter, by reference to the performance of a range of synthesised block copolymers as cold flow improvers for diesel fuel.

Worked Example 3—Synthesis of Diblock Copolymers and Performance as Fuel Additives Based on the general worked example above, examples of diblock copolymers were made as shown in the table below, in each case starting from the specified compound (II) produced in step a) of the reaction as shown.

In each case, the diblock polymer produced was thereafter tested for its ability to improve (i.e. lower) the cold filter plugging point temperature ("CFPP" temperature) of a base diesel fuel having an untreated CFPP temperature of each case, the polymer was added to the base fuel via the preparation of an additive concentrate of the invention, involving the physical mixing of the polymer and organic carrier liquid (aromatic solvent) using a laboratory rotary blender, and thereafter doped into the fuel in varying amounts to determine the fuel's response to the additive in each case.

As can be seen from the results, the polymers of the invention, when used as additives for diesel fuel, brought about significant improvements in the cold flow behaviour over the base fuel, as evidenced by the depression of the cold filter plugging point (CFPP) temperature in the range of tests shown. As a result, the treated fuels are less likely to give rise to problems of filter blocking after periods of cold storage, or during use at cold temperatures.

Results (base fuel CFPP=−10° C.)

| Compound (II) | Metallating reagent | Monomer for anionic polymerisation | Product formed | Treat rate of product in diesel fuel (ppm, wt/wt) | CFPP temperature (° C.) |
| --- | --- | --- | --- | --- | --- |
| PE-t-DIB* | n-BuLi | styrene | PE-DIB-PS | 200 | −13 |
|  |  |  |  | 300 | −17 |
|  |  |  |  | 400 | −16 |

-continued

| Compound (II) | Metallating reagent | Monomer for anionic polymerisation | Product formed | Treat rate of product in diesel fuel (ppm, wt/wt) | CFPP temperature (° C.) |
|---|---|---|---|---|---|
| PE-t-DIB* | n-BuLi | tert-butyl styrene | PE-DIB tBS | 200 300 | −17 −20 |
| PE-t-DIB* | n-BuLi | Tert-butyl methacrylate | PE-DIB-tBMA | 200 300 400 | −17 −16 −14 |
| PE-t-DIB* | n-BuLi | isoprene | PE-DIB-PI | 200 300 400 | −17 −18 −20 |

*polyethylene terminally functionalised with 1,3-DIB (diisopropenylbenzene)

From the results, it is evident that the diblock copolymer functions in its own right as a cold flow improver.

The determination of the improvement at a range of treat rates allows the skilled person to draw conclusions about the necessary amount of each additive required to provide optimum (or other target) performance when employing the method and use of the invention.

What is claimed is:

1. A process for manufacture of a functionalised diblock copolymer comprising 2 polymeric blocks wherein:
   (i) the first block consists of a chain of ethylenic structural traits, optionally interrupted by one or more structural units derived from 1-alkene co-monomers higher than ethylene, and
   (ii) the second Hock comprises a chain of structural units derived from one or more α,β-unsaturated monomers selected from styrene, substituted styrene, acrylate, methacrylate and diene compounds, and wherein said first and second Hocks of the copolymer are terminally joined by means of the following structural linkage:

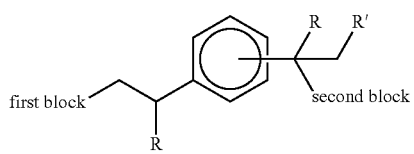

wherein each R group independently represents an alkyl or aryl group and R' represents hydrogen or an alkyl group, and wherein the aromatic ring substituent joined to the second block is positioned meta or para to the aromatic ring substituent joined to the first block;

the process comprising the following steps:
   a) in a first step, polymerising ethylene, and optionally one or more 1-alkene co-monomers higher than ethylene, in the presence of a metallocene catalyst system to form a first polymer block, being a chain consisting of ethylenic structural units optionally bearing pendent alkyl groups originating from 1-alkene comonomer(s), the reaction being carried out in solution at a temperature of at least 50° C. in the presence of a compound of the formula (I):

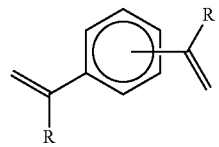

in a reaction vessel pressurised with hydrogen gas, wherein, in the course of the reaction, the compound (I) is terminally incorporated onto the first polymer block resulting in the formation of a terminally unsaturated intermediate of the formula (II):

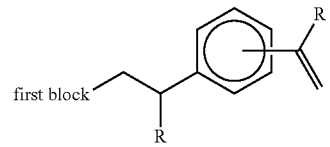

b) in a second step, recovering the intermediate (II) from the reaction mixture of the first step; and
   c) in a third step, reacting the intermediate (II) at its terminal double bond in a subsequent polymerisation reaction to form a second polymer block, so yielding a diblock polymer of the structure defined above.

2. The process of claim 1, wherein the compound (I) has the structure:

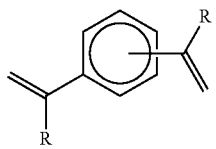

wherein each R group independently represents an alkyl group having from 1 to 4 carbon atoms.

3. The process of claim 2, wherein the compound (I) has the structure:

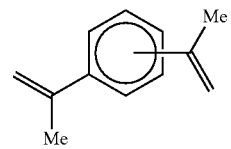

4. The process of claim 1, wherein R' represents n-butyl.

5. The process of claim 1, wherein, in the compound of formula (I), the aromatic ring substituent joined to the second block is positioned meta to the substituent joined to the first block.

6. The process of claim 1 wherein the third step c) is an anionic polymerisation reaction, wherein the terminal double bond of the intermediate of formula (II) is reacted with a metallating reagent to form an anion which initiates polymerisation therefrom upon the addition of one or more α,β-unsaturated monomers selected from styrene, substituted styrene, acrylate, methacrylate and diene compounds.

7. The process of claim 6, wherein the metallating agent is an alkyl metal compound R'M and the intermediate of the formula (II) has the structure:

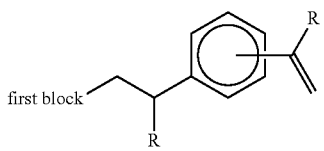

wherein each R group independently represents an alkyl group having from 1 to 4 carbon atoms; and wherein, in the course of the third reaction step c), the alkyl group R' of the alkyl metal compound inserts onto the less-substituted carbon of the double bond, giving rise to a reactive anionic intermediate having the structure of the formula (III):

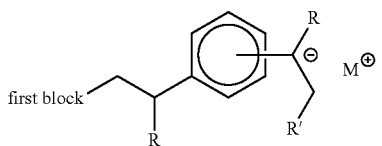

(III)

wherein alkyl represents the inserted alkyl group originating from the alkyl metal compound, $^{(-)}$ represents the metallated carbanionic site from which the anionic polymerisation of the third reaction step thereafter proceeds, and $M^{(+)}$ represents the metal cation originating from the metal M of the alkyl metal compound.

8. The process of claim 6 wherein the metallating reagent comprises n-butyl lithium or sec-butyl lithium.

9. The process of claim 6 wherein the intermediate of the formula (II) has the structure

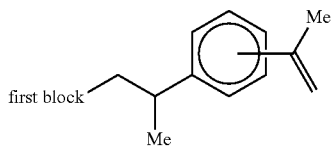

and the metallating reagent comprises n-butyl lithium.

10. The isolated intermediate compound of the formula (II):

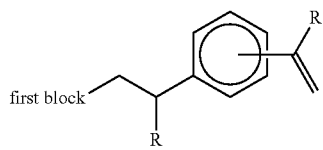

(II)

wherein each R group independently represents an alkyl or aryl group, and wherein the aromatic ring substituent —C(R)═CH$_2$ is positioned meta or para to the substituent joined to the first block.

11. The anionic intermediate of the formula (III):

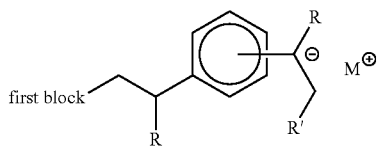

wherein each R group independently represents an alkyl or aryl group and wherein the aromatic ring substituent —C$^{(-)}$(R)—CH$_2$(R') is positioned meta or para to the aromatic ring substituent joined to the first block; wherein R' represents an alkyl group and M$^+$ represents a metal cation, and C$^{(-)}$ represents a metallated carboanionic site.

12. The intermediate of claim 10 wherein each R group independently represents an alkyl group having from 1 to 4 carbon atoms.

13. The intermediate of claim 12 wherein each R group independently represents a methyl group.

14. The intermediate of claim 13 wherein R' represents n-butyl.

15. The intermediate of claim 14 wherein the other aromatic ring substituent is positioned meta to the substituent joined to the first block.

16. The intermediate of claim 15 wherein the first block consists of a polyethylene chain.

17. The intermediate of claim 16 wherein the first block has a number average molecular weight (Mn), as measured by GPC against polystyrene standards, in the range of 500 to 20000 g mol$^{-1}$.

18. The intermediate of claim 11 wherein each R group independently represents an alkyl group having from 1 to 4 carbon atoms.

19. The intermediate of claim 18 wherein each R group independently represents a methyl group.

20. The intermediate of claim 19 wherein R' represents n-butyl.

21. The intermediate of claim 20 wherein the other aromatic ring substituent is positioned meta to the substituent joined to the first block.

22. The intermediate of claim 21 wherein the first block consists of a polyethylene chain.

23. The intermediate of claim 22 wherein the first block has a number average molecular weight (Mn), as measured by GPC against polystyrene standards, in the range of 500 to 20,000 g mol$^{-1}$.

24. The anionic intermediate (III) of claim 11, wherein M$^+$ represents a lithium cation.

* * * * *

UNITED STATES PATENT AND TRADEMARK OFFICE
CERTIFICATE OF CORRECTION

PATENT NO. : 9,845,375 B2  
APPLICATION NO. : 15/368868  
DATED : December 19, 2017  
INVENTOR(S) : Carl Waterson et al.

Page 1 of 1

It is certified that error appears in the above-identified patent and that said Letters Patent is hereby corrected as shown below:

In the Claims

Claim 1 (i), Line 4, delete "traits" and insert -- units --.

Claim 1 (ii), Line 7, delete "Hock" and insert -- block --.

Claim 1, Line 11, delete "Hocks" and insert -- block --.

Claim 11, last line, delete "carboanionic" and insert -- carbanionic --.

Signed and Sealed this  
Twenty-seventh Day of February, 2018

Andrei Iancu  
*Director of the United States Patent and Trademark Office*